(12) United States Patent
Dubrul

(10) Patent No.: US 6,258,115 B1
(45) Date of Patent: *Jul. 10, 2001

(54) BIFURCATED STENT AND DISTAL PROTECTION SYSTEM

(75) Inventor: William Richard Dubrul, Redwood City, CA (US)

(73) Assignee: Artemis Medical, Inc., San Mateo, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/063,735

(22) Filed: Apr. 21, 1998

Related U.S. Application Data
(60) Provisional application No. 60/044,163, filed on Apr. 23, 1997.

(51) Int. Cl.$^7$ ............................................. A61M 29/00
(52) U.S. Cl. ............................................. 606/200; 606/191
(58) Field of Search ..................................... 606/200, 191

(56) References Cited

U.S. PATENT DOCUMENTS

| | | | |
|---|---|---|---|
| 3,996,938 | 12/1976 | Clark, III | 128/348 |
| 4,611,594 | 9/1986 | Grayhack et al. | 128/328 |
| 4,650,466 | 3/1987 | Luther | 604/95 |
| 5,030,201 | 7/1991 | Palestrant | 604/22 |
| 5,102,415 | 4/1992 | Guenther et al. | 606/159 |
| 5,382,259 | 1/1995 | Phelps et al. | |
| 5,383,892 | 1/1995 | Cardon et al. | |
| 5,507,769 | 4/1996 | Marin et al. | |
| 5,562,725 | 10/1996 | Schmitt et al. | |
| 5,591,227 | 1/1997 | Dinh et al. | 623/1 |
| 5,603,722 | 2/1997 | Phan et al. | |
| 5,643,282 | 7/1997 | Kieturakis | 606/114 |
| 5,720,764 | * 2/1998 | Naderlinger | 606/200 |
| 5,769,816 | * 6/1998 | Barbut et al. | 604/96 |
| 5,792,157 | 8/1998 | Mische et al. | 606/159 |
| 5,814,064 | * 9/1998 | Daniel et al. | 606/200 |
| 5,827,324 | * 10/1998 | Cassell et al. | 606/200 |
| 5,868,708 | 2/1999 | Hart et al. | 604/104 |
| 5,928,260 | * 7/1999 | Chin et al. | 606/200 |
| 5,928,261 | * 7/1999 | Ruiz | 606/200 |
| 6,027,520 | 2/2000 | Tsugita et al. | 606/200 |
| 6,053,932 | * 4/2000 | Daniel et al. | 606/200 |
| 6,086,605 | * 7/2000 | Barbut et al. | 606/200 |
| 6,096,053 | * 8/2000 | Bates | 606/159 |

FOREIGN PATENT DOCUMENTS

| | | |
|---|---|---|
| 39 13935 | 4/1989 | (DE) . |
| 2020557 | 11/1979 | (GB) . |

* cited by examiner

Primary Examiner—David H. Willse
Assistant Examiner—Suzette J. Jackson
(74) Attorney, Agent, or Firm—James F. Hann; Waynes & Beffel LLP

(57) ABSTRACT

A stent comprising varying porosity's for use in vessels with bifurcations or side branches. The stent allows for scaffolding of the stenotic area but still allows for flow into the side branches. A distal protection system is also described.

9 Claims, 6 Drawing Sheets

BIFURCATED STENT AND DISTAL PROTECTION SYSTEM

CROSS REFERENCE TO RELATED APPLICATION

The present invention is a continuation of provisional patent application serial No. 60/044,163, filed on and claiming priority of Apr. 23, 1997, the full disclosure of which is incorporated herein by reference.

BACKGROUND OF THE INVENTION

1. Field of the Invention

The present invention relates to an implarnable intraluminal device. More specifically, the present invention relates to an implantable intraluminal device which is particularly useful for repairing or serving as a conduit for vessels narrowed or occluded by disease or for use in other body passageways requiring reinforcement or the like. Further, devices are disclosed in the present invention that can trap particulate that is loosened during interventional procedures such as stent or stent-graft placement, angioplasty, atherectomy, etc.

2. Description of Background Art

Intraluminal devices or, more specifically, endovascular prostheses, are known for treating stenosis, stricture, aneurysm conditions and the like. Often these devices are implanted via LIS (Least Invasive Surgery); whereby a small percutaneous access into the vessel is accomplished (usually remote to the diseased area). Alternatively, they are installed via an 'open surgery' approach. Advantages of the LIS approach (over conventional surgery) are significant from a cost as well as a patient care and recovery point of view. Intraluminal scaffolding devices such as stents are often used in combination with grafts and vice versa. The graft is usually, but not always a textile/fabric type device that is used to cover a greater area of the scaffolding as well as aid in neo-intimal formation after placement. Further, the two (stents and grafts) are often designed into one device called a stent-graft.

Each year about half a million Americans suffer a stroke in which obstruction or hemorrhage impairs the crucial flow of blood to the brain. About 150,000 of these stroke victims die, making stroke the third leading cause of death after heart disease and cancer, and many more suffer permanent disability. According to the American Heart Association the cost of treating stroke exceeds $25 billion a year.

Currently, approximately 180,000 Americans undergo a preventative operation to clear carotid arteries that carry blood to the brain. The operation, known as Carotid Endarterectomy (surgical removal of plaque from the carotid artery), usually requires patients to stay in the hospital a few days, with typically a few weeks recovery time. This surgical procedure is increasing at an annual rate of greater than 20%.

A debate has arisen between vascular surgeons and "interventional" cardiologists and radiologists concerning the advantages of using of stents and/or stent-grafts to treat occluded carotid arteries compared with surgery. Stroke prevention operations/surgeries like endarterectomies are performed by vascular surgeons in the United States at a cost of about $1.5 billion per year. Efforts to use small stents in the brain to open and maintain patency in clogged arteries have triggered a fierce debate comparing the safety and efficacy of the medical techniques. Interventionalists claim that the scaffolding accomplished with stents is easier on the patient and the patient's pocketbook. Surgeons, on the other hand, are skeptical of stenting in the carotid because of the potential for neurological complications as well as the potential for the stent to 'recoil' (return to a smaller diameter than when originally placed) some time after initial placement.

Various strategies have been devised and developed for vascular intervention in the treatment of Chronic Occlusive Disease (COD). Much of the critical occlusive disease occurs at junctions (bifurcations) in the vasculature. Of particular interest are occluded carotid arteries and other bifurcated vasculature junctures.

A recent study funded by the NIH indicates the incidence of stroke can be reduced by 55% if the occluded carotid is treated by surgical intervention. This surgical procedure sometimes allow minute pieces of plaque or blood clot (emboli) to travel into the brain causing at least temporary neurological damage, and often stroke or permanent neurological defects.

Various devices have been devised and used to dispense thrombolytic agents to the occluded vasculature and/or physically disrupt and dislodge the occluding thrombus. One such catheter, described in U.S. Pat. Nos. 5,498,236, 5,380,273, and 5,713,848 by the present inventor was developed to penetrate and cross occluded portions within the vasculature, deploy an occlusion device distal to the occlusion to stop emboli from iatrogenic damage while clearing the occlusion/blockage. Although such catheters are adequate for removing occluding tissue in a vessel lumen, restenosis occurs unless balloon angioplasty or some sort of scaffolding is left in place to prop the vessel open (e.g. stent or stent-graft). Scaffolding is becoming a preferred treatment, usually with balloon angioplasty (or sometimes without) because balloon angioplasty when used without some type of scaffolding has a tendency to have a temporary result.

Femoral artery access allows the interventionalist an easy, safe and less costly approach to treat carotid stenosis with the least invasive trauma to the patient (other access is used as well). However, the need arises for a stent that can be deployed at a vascular "bifurcation" which does not occlude the side tributary (or side branch) at the bifurcation and still provide sufficient radial force to keep the vessel sufficiently open. In other words, a multi-porous or bifurcated stent or stent-graft that provides scaffolding at the vascular bifurcation and still allows blood to flow in the main vessel as well as into the bifurcated tributary is desirable.

The prior art regarding scaffolding or 'propping open' of closed or stenotic vessels is extensive. Stents or stent-grafts for scaffolding singular lumens (without bifurcations) are numerous. Stents in the past decade have been one of the most prominent technologies dealing with occlusive vascular disease. Additionally stents or stent-grafts for non-vascular occlusions such as urological, esophageal, biliary, etc. are prevalent as well. U.S. Pat. No. 5,383,925 by Schmitt et al describe a three dimensional braided soft tissue prostheses. In and of itself; this invention has similarities to the present invention because the present invention also discloses braided prostheses (as well as a non-braided prosthesis). However, Schmitt et al does not address the subject of tributaries and bifurcations. Similarly, U.S. Pat. No. 5,366,505 by Anderson et al describe a tubular medical prosthesis with knitted filaments with openings in between the filaments. This patent also does not address scaffolding of bifurcations. The stent or scaffolding intellectual property of this type that do not address stenting of bifurcations is extensive and will not be further addressed in this patent.

Conversely, endovascular support devices that address this scaffolding or stenting of bifurcations although much less common than the aforementioned non-bifurcated stents or stent-grafts are also prevalent in the market of stents as well in the patent theatre. For example U.S. Pat. No. 5,718,724 by Goicoechea et al describe a bifurcated endoluminal prosthesis and method of installing the device, whereby the stent is configured into a one or two part Y configuration. In an analogous U.S. Pat. No. 5,632,763 by Glastra et al; the bifurcated stent in this patent is also an Y shaped scaffold. In these and similar Y shaped/configured bifurcated stents, the stent is designed to be placed in the entire bifurcation or Y. This enables scaffolding of the entire junction of all three tributaries.

However, there are situations where only the main vessel of the tributary is required to be stented. Such appears to be the case of stenting the bifurcation of the carotid artery. Thousands of linear (as opposed to Y stents) stents have been placed without FDA approval in the U.S. in this bifurcated carotid area. In these cases, a stent is placed into the common carotid artery and further into the internal carotid artery. The stent is placed across the external carotid artery. These stents have walls with a very 'open' structure in that they are braided stents but have large enough areas to allow blood to flow through the stent wall and into the external carotid artery or other side branch These numerous implantations have been reported without significant complications however at the time of this invention, prospective and long-term studies have not been completed. Blood flow from the common carotid artery and into the internal carotid artery appears to be more important due to the fact that the internal carotid artery feeds blood into the middle cerebral artery and other arteries of the brain. However, blood flow into the external artery is still important and has to pass through the stent wall. This is known as 'stent jail' because the blood has to pass through the weaves/filaments of the stent. Because of this phenomenon, only stents with large openings between the filaments of the stent can be used. This creates another problem in that there is a direct correlation between the openings between the filaments (pics per inch) and the outward radial force that can be transmitted to the vessel wall. As this open space increases, the outward radial force of the stent decreases. Conversely as the openings decrease in size, the radial force increases. Hence it is the object of the present invention to obviate that disadvantage by designing a multi-porous stent for bifurcations that allow a sufficient outward radial force, but still allows flow into the tributary or side branch U.S. Pat. No. 5,607,444 by Lam describes an ostial stent for bifurcations that is different than the Y configuration in that it the main tubular body of the stent is seated into the side branch and has a flaring end that is attached into the main vessel thereby not obstructing flow of the main branch This design may be useful for side branches, but does not address the main vessel.

As previously mentioned, emboli can become loosened during surgical endarterectomies and these emboli can have deleterious affects 'downstream'. This occurrence would appear to be increased with a LIS approach due to the fact that in an open procedure, the site of revision is in direct view so that these particulate should be more easily detected Conversely in a LIS procedure the physician is dependent upon image intensification and his or her actual skill to not allow emboli from being dislodged and causing 'downstream', distal problems. U.S. Pat. No. 5,695,519, by Summers et al, describes a percutaneous filter for carotid angioplasty. This design disclosure appears to have merit, but by design, it has a membrane of filter material that is overlapping that increases its diameter prior to deployment and upon un-deployment. The present invention obviates this disadvantage of a larger diameter in that there are no overlapping filaments. Further, a cumbersome 'gun' is required with the Summer system. Even further, the system is used only with angioplasty, which, as previously mentioned has a temporary effect. U.S. Pat. Nos. 4,842,579 and 4,926,858 describe distal barriers associated with atherectomy devices. Atherectomy has fallen from favor due to its apparent lack of efficacy combined with the complexity of use as compared with stent or stent-graft placement. Certainly, these devices have not been perfected nor attempted for use in the head in neck area. The filter/trap/occluder device of the present invention is designed to be used alone without any angioplasty, atherectomy device. Further, the present filter invention has been fabricated and tested where diameters of the device are as small as 0.010 inches in diameter. With sizes this small and smaller, use in the vasculature of the head, is now available. This area appears to be the new and large frontier in the treatment COD. Further, the filter/trap/occluder system of the present invention provides for a novel braiding technique (that is used in the bifurcated stent or stent-graft as well) that allows for entrapment of particles and removal.

SUMMARY OF THE INVENTION

A "procedure" oriented system for carotid stenting is presented which reduces or eliminates the stroke potential during stent placement by positioning a fragment filteritrap/occluder downstream (distally) from where the stent is disposed within a bifurcated blood vessel such as the common carotid artery. The stent or stent-graft can be positioned and deployed with comfort knowing that any clot, tissue fragments, etc. (emboli) which are mobilized during deployment of the stent will be trapped in the filter thereby preventing such fragments from entering the brain vasculature and causing the aforementioned deleterious effects.

Often the stenosis in the carotid occurs at the junction of the common, internal and external carotid arteries. This point of bifurcation of the common carotid artery is difficult to stenr. The present invention includes both a single lumen, multi-porous stent and a biflircated stent, both of which are operable for stenting, the common carotid artery at its point of bifurcation. The present invention is also useful for scaffolding (propping open) other bifurcated areas of the body, both vascular and non-vascular.

It is an object of this invention to provide a stent for mantnig patency of two or more branches of a bifurcated blood vessel that may be positioned using LIS at the point of bifurcation. These stents or stent-grafts can also be placed witihan 'open' surgery approach.

It is a further object of the invention to provide an intravascular catheter for deploying a stent.

It is yet a further object of the invention to provide a stent deployment catheter or guide wire having filter means thereon operable for trapping tissue fragments dislodged during interventional procedures such as stent or stent-graft placement, balloon angioplasties, thrombolysis, etc.

It is still a further object of the invention to provide a stent or stent graft for a bifurcated blood vessel which does not substantially interfere with the flow of blood through side branch vessel The features of the invention believed to be novel are set forth with particularity in the appended claims. However, the invention itself, both as to organization and method of operation, together with further objects and advantages thereof may best be understood by reference to the following description taken in conjunction with the accompanying drawings.

BRIEF DESCRIPTION OF THE DRAWINGS

FIG. 1 is also interpreted as being any vessel within the body where a bifurcation exists. It does not represent only the common carotid artery.

FIG. 4 illustrates both a ribbon type multi-porous stent or stent-graft (4C & 4D) and a braided type multi-porous stent or stent-graft (4A & 4B).

FIG. 5 shows the un-deployed stent or stent-gaf being inserted into position (5B), deployed and then the filter system removed (5C).

DESCRIPTION OF THE EXEMPLARY EMBODIMENTS

Figure 1:
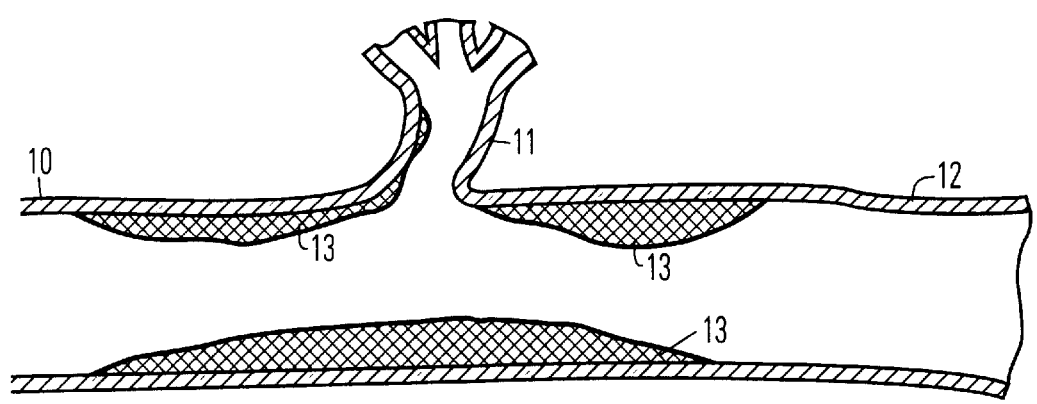
FIG. 1 is a twodiensional schematic cross-sectional view of the common carotid artery bifurcated to form the external carotid and the internal carotid arteries with a stenosis within both branches.

The vasculature comprising the common carotid artery is shown schematically in FIG. 1. The common carotid artery 10 branches to form the external carotid artery 11 and the internal carotid artery 12. The walls 13 of the commnon carotid artery and the internal carotid are shown in FIG. 1 to be thickened, reducing the lumen diameter of the vasculature. This thickened wall is often referred to as a stenotic lesion of the vessel and inhibits flow through the vessel.

Figure 2A:
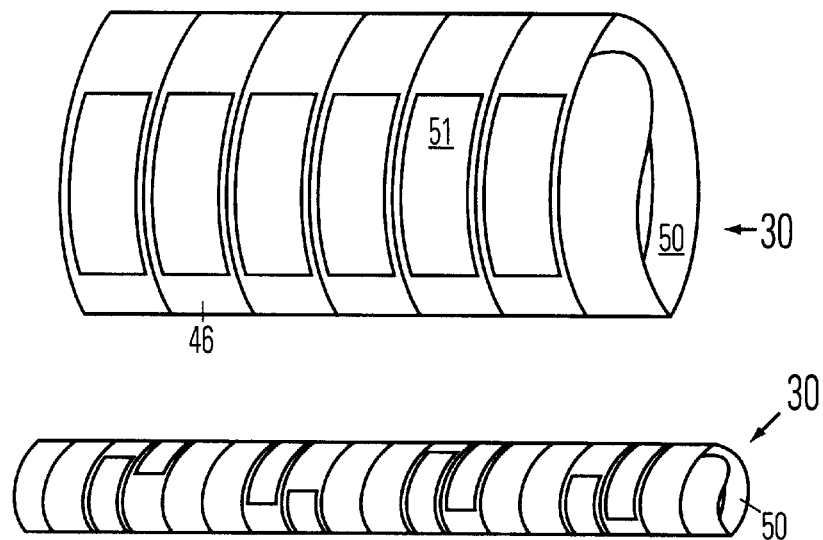
FIG. 2 is a three-dimension perspective of two particular scaffolds of the present invention. In these schematics, the scaffold (stent or stent-graft) is made from a flat ribbon type material.
Figure 2B:
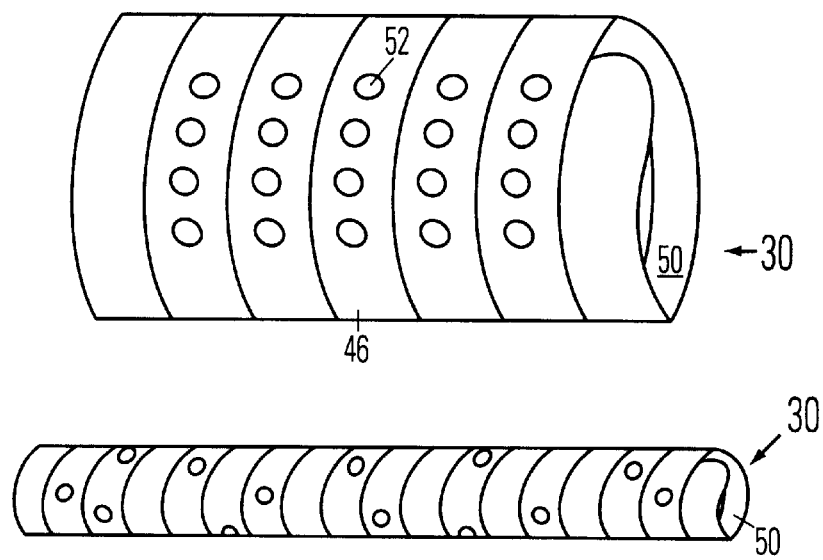
Figure 3A:
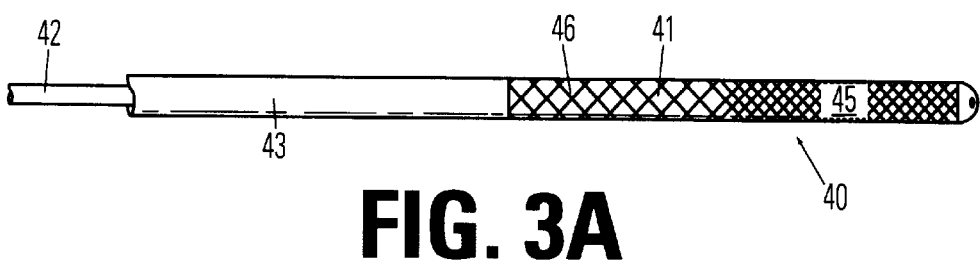
FIG. 3 is a two-dimensional illustration of the distal protection filter/trap/occluder that may be used prior to or with placement of the stent. Further this distal protection system can be used in any interventional procedure where distal protection is desired.
Figure 3B:
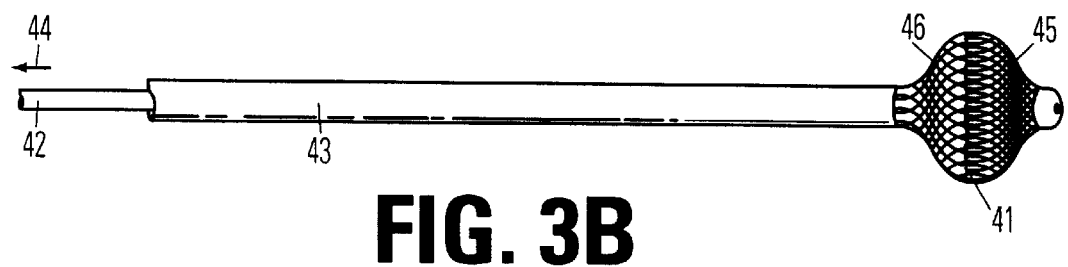
Figure 4A:
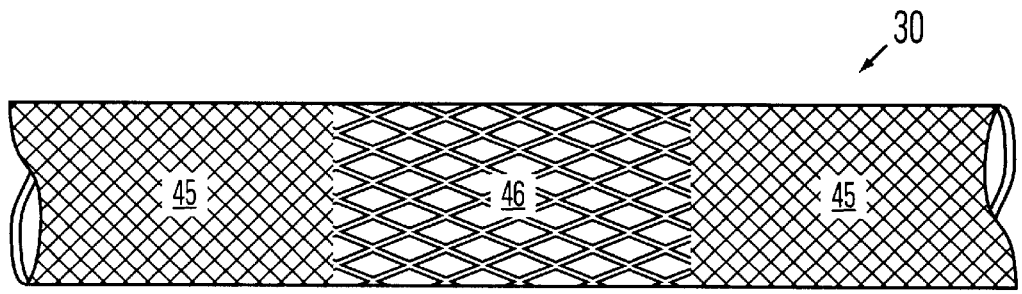
FIG. 4 shows two-dimensional illustrations of the scaffolding described in the present invention.
Figure 4B:
Figure 5A:
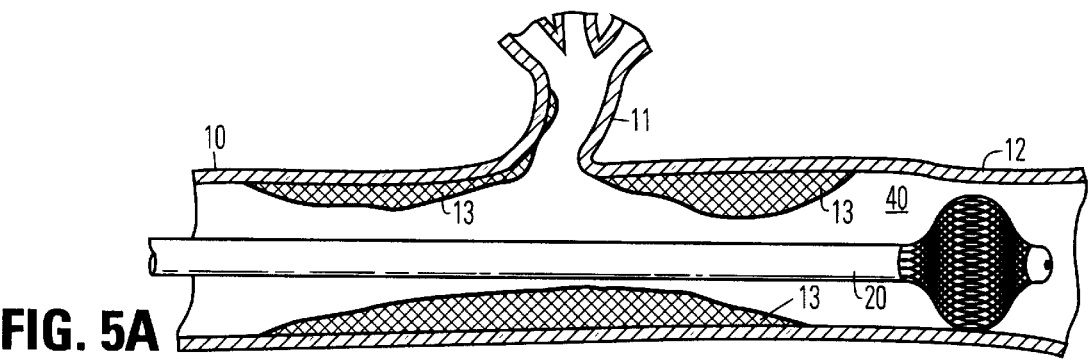
FIG. 5 shows the bifurcated vessel in accordance with FIG. 1 wherein the filter is first inserted and then deployed in the vessel (5A). Further
Figure 5B:
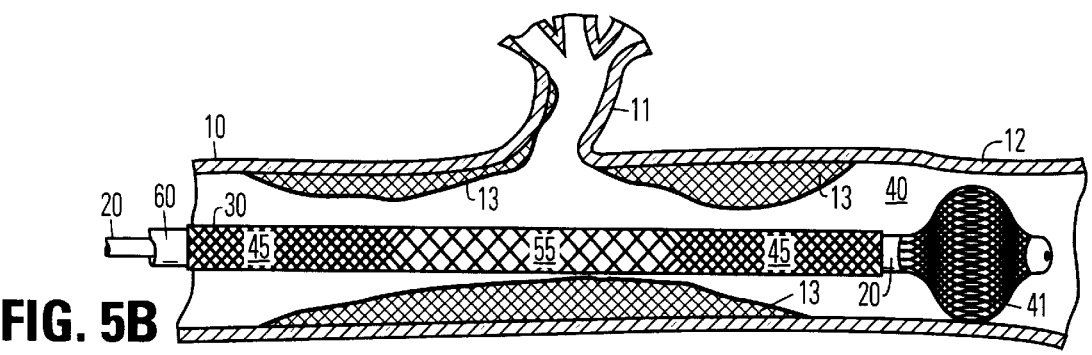
Figure 5C:
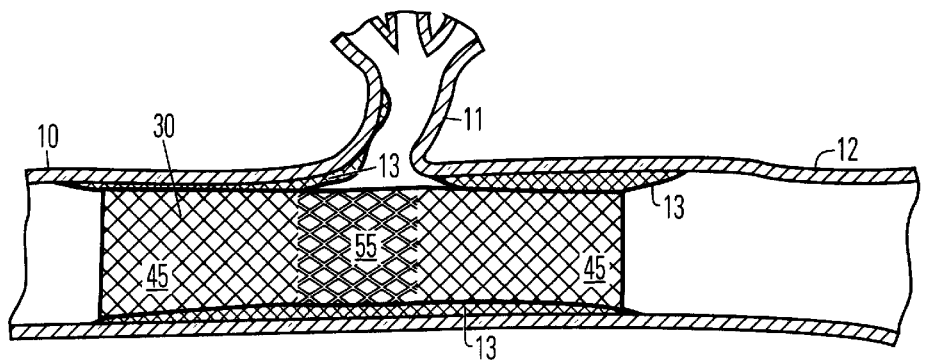
Figure 6A:
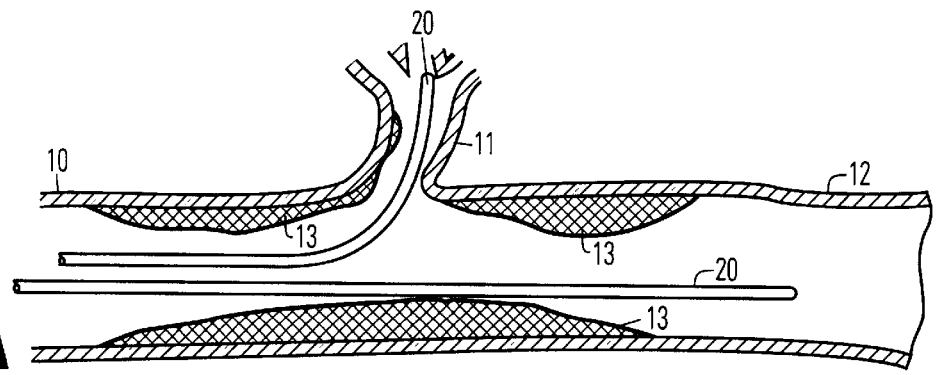
FIG. 6 shows the bifurcated vessel in accordance with FIG. 1 wherein two guide wires are inserted into the main and branch vessel (6A), the bifurcated stent or stent-graft of the present invention is inserted into the bifurcated area (6B & 6C), deployed and then the guide wires are removed (6D).
Figure 6B:
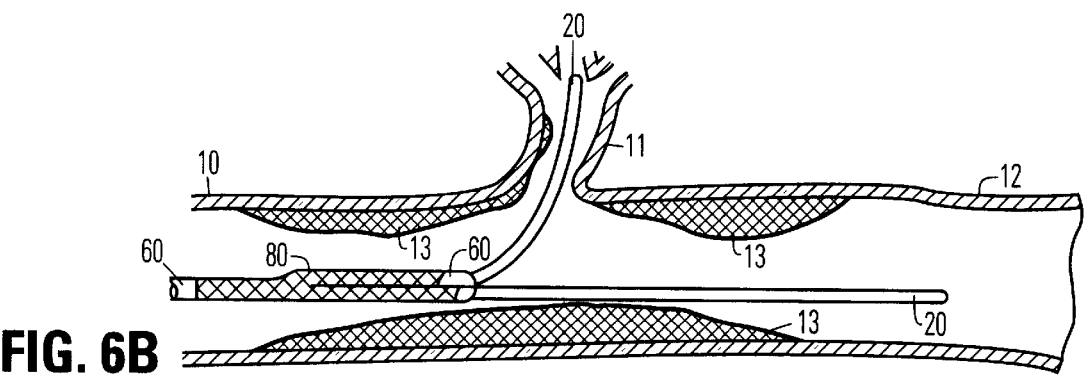
Figure 6C:
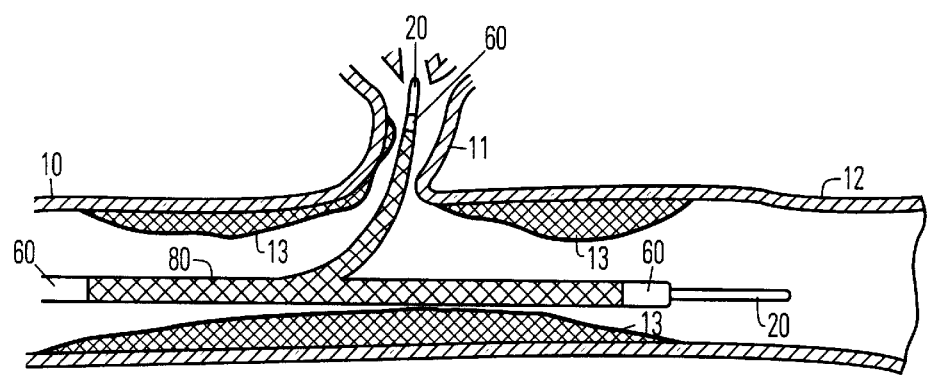

A guide wire 20 may be positioned within the stenosed lumen of the common, internal and/or external carotid arteries (or other bifurcated vessel system) as shown in FIGS. 5A, 5B, 6A, 6B & 6C. In FIGS. 6A, 6B & 6C, two guide wires 20 have been placed. A stent, which can be placed in any bifurcated lumen within the body (e.g. vascular, gastrointestinal, esophageal, etc.), is referred to herein as a "Multi-porous stent" and shown at 30 in FIGS. 2,4 & 5. Turning now to FIG. 3, the filter 40 comprises a braided structure that is attached to an inner mandrill or wire 42 and an outer tube 43. The braid 41 is attached to the distally to the inner wire 42 and proximally to the outer tube 43. This attachment is accomplished in many ways, welding. heat-staking, gluing, etc. In FIG. 3A, the filter 40 is in the undeployed configuration. In FIG. 3B, the filter 40 is in the deployed condition. This is accomplished by moving the inner wire 42 with respect to outer tube 43 and can be shown by the arrow 44 in FIG. 3B. This action causes the braid to be put into compression and forces it to expand in an outward direction as in FIG. 3B. The filter 40 illutrated is one which has variable pics per inch. One way to fabricate this variable braid is described in U.S. Pat. No. 5.366,443 by Eggars et al. This principal is often referred to as MLIB (Multi-Layer Interlocking Braid), but this variable braid configuration can be made other ways, only one of which is by merely compressing the braid in an asymmetrical fashion. Another way is to attach two different braids together during manufacturing. The stent or stent-graft 30 of FIGS. 4A, 4B, 5B & 5C may be manufactured using this variable braid technology. The filter 40 can be made from simple non-variable braid as well. In that situation, the filter 40 is deployed in the vessel and may or may not allow flow through it. If particulate are dislodged during the procedure, they will be trapped from moving downstream and can be irrigated/aspirated/lysed/obliterated (removed) from the vessel prior to un-deploying the filter and removal of it. Alternatively, the distal part of the filter 40 can have a covering over it that allows only small particles pass that are not detrinental. This covering can be a porous elastic membrane, other braid, film, filter, fabric, textile, etc. In any case, the filter 40 may have one pore size on the proximal side of the filter 40 and a smaller pore size on the distal end. This will allow particles to travel into the proximal pores (in the case of braid, the interstitial space between the filaments), become trapped inside the filter 40 and then upon un-deployment removed from the vessel and patient. Turning now to FIG. 4A & 4B, the multi-porous stent or stent-graft can be designed in a similar fashion to the MLIB filter 40 previously described. Alternatively, as with filter 40, this multi-porosity can be altered using fabric, membrane, etc. Further, it can be fabricated by attaching two different types of braided structure together during manufacturing. In FIGS. 3A, 3B, 4A & 4B, the smaller pore size is represented by 45 and 46 show the larger pore size. All stents 30 in can be metal or non-metal, as can the filters/traps/occluders. In the case of a self-expanding stent or filter, the material may be shaped memory alloy (SMA, metallic or polymeric). It is important to note that in FIGS. 3 & 5, the filter/trap/occluder illustrated can also be the initial guide wire(s) 20 placed or they can be an additional filter/trap/occluder 40. This filter/trap/occluder may be placed over the initially placed guide wire 20 whereby it will have an additional inner lumen. In that case, the inner mandrill 42, would be a tubular structure as well. Further, the filter/trap/occiuder can be placed all by itself Turning now to FIGS. 2A, 2B, 4C & 4D, the multi-porous stent illustrated there is made of flattened material or ribbon 50. The multi-porous characteristic is constructed by removing part of the ribbon material from the ribbon 50. This removed material is illustrated as windows 51 and 52 in the drawings. In FIG. 4, the windows 51 are longitudinally shaped with respect to the ribbon 50. In FIG. 2B, the windows 52 are in a circular shape. It is recognized that the shape of these openings is not relevant to the present invention, as any shape will result in multi-porosity. The ribbon 50 can be made of metallic or non-metallic material. In the case of self-expanding stents, the material may be made of shaped memory alloy (SMA, metallic or polymeric). The strip of SMA is wound into a helical shape having a small diameter dimensioned to fit within the vessel. When the stent material is a shape memory alloy (such as Nitinol, NiTi Nickel-Titanium or other similarly acting material) it can be programmed so that when heated from a cool temperature (e.g. room temperature) to body temperature (37° C., 98° F.) it will assume a programmed, expanded tubular shape shown in FIGS. 5C & 6D or as illustrated in FIGS. 2, 4A, 4C, 5C & 6D. The shape-memory stent or stent-graft (or filter) material is chosen such that the transition temperature between the smaller, deformed structure shown in FIGS. 2A, 2B, 3A, 4B, 4D, 5B, 6B and 6C and the large diameter tubula structure shown in FIGS. 2A, 2B, 4A, 4C, 5C and 6D occurs at or below body temperature (or some other temperature differential that will facilitate the change in size). The change in shape of the SMA material can be accomplished by the body temperature (whereby it would need to be constrained until in position) or by an extraneous thermal source such as warmed saline or a thermal catheter or guide wire. It is well known to anyone skilled in the art that SMA may need an elevated temperature to effect its dimensional change, but it will retain that changed configuration with a temperature lower than that required to create the change in the first place. In other words, the stent 30 or filter 41 may need some temperature higher than body temperature (37° C. or 98° F.) like 35° C. or 110° F. to expand, but will stay expanded with significant radial force at the lower body temperature. The stent 30 or filter 40 is preferably coated with a medical grade substance having low thrombogenicity or other medicament that helps prevent deleterious effects that may accompany these procedures. Alternatively, the stent 30 may be coated with any of a variety of fabrics/textiles that allow tissue growth into it and/or other stabilization. Further, the stent 30 may be impregnated with radioactivity, monoclonal anti-bodies or a variety of other medicaments that may inhibit restenosis or other deleterious effects that wish to be avoided. Even further, it is understood that use of the present invention can be used with image intensification (Fluoroscopy, Ultrasound, Intraluminal Ultrasound, etc.).

Further, the stent 30 can be deployed by means of a guide wire or by means of an intravascular balloon catheter used either alone or adapted to slide over a guide wire 20, as will be discussed below. The stent 30 is advanced along the guide wire 20 until it is in position at the juncture between the conmon and the internal carotid arteries (or other bifurcated vessel) as shown in FIGS. 5 & 6. It is recognized that the filter 40 also referred to as Distal Protection System (DPS) may or may not be used in conjunction with the stent placement. A guide wire 20 only may be used with a stent delivery catheter 60. Alternatively, a guide wire 20 and filter 40 and delivery catheter 60 could be used. Another alternative would be the filter 40 and the stent 30 only could be used. Further, filter 40 and catheter 60 alone could be used.

Figure 6D:
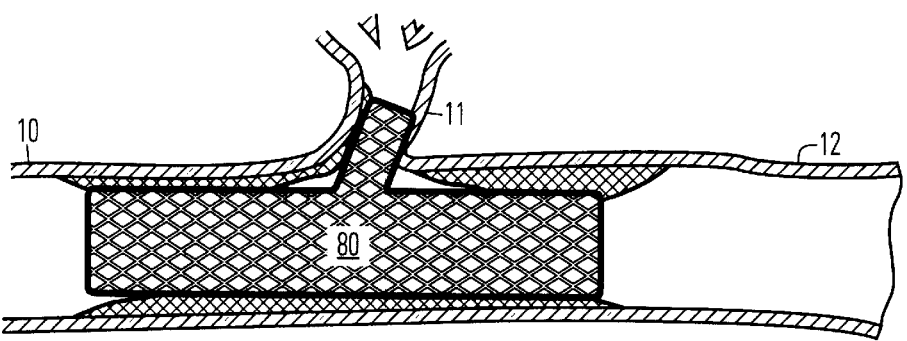

At this point (when SMA is used), the stent 30 is permitted to warm to body temperature whereupon the stent undergoes a shape transformation as shown in FIG. 5C or 6D. Alternatively, as mentioned above, additional thermal energy could be delivered to that area Even further, SMA may not be used and the stent 30 could be deployed using an inflatable balloon (not shown) or other outward radial force component to enlarge the stent 30. The increased diameter of the stent holds the carotid artery (or other vessel) open at the juncture between the internal and common carotid arteries (or other vessel). A portion of the stent 55 or 46 is preferably more permeable to flow than the remaining portion of the stent 45. This may be accomplished by aligning the windows 51 or 52 in the stent 30 such that upon enlarging the stent, the holes are preferably positioned with respect of the external carotid artery (or other side branch). Alternatively in the case of FIG. 5B and 5C, the multi-porous stent will be positioned so that the larger pores 55 are oriented to the side branch The guide wire and/or catheter are then removed and the stent remains in position until no longer needed.

Another approach to maintaining patency at the point of bifurcation of the carotid is by deploying a bifurcated stent. The bifurcated stent 80 (FIGS. 6 B, C &D) can also be made self-expanding from a shape-memory alloy or balloon expandable. The bifurcated stent 80 may be conveniently positioned at the juncture by means of dual guide wires as shown in FIG. 6. The pair of guide wires 20 are advanced through the common carotid artery (or other vessel) until they reach the bifurcation point. One guide wire 20 is inserted and advanced into the external carotid artery (or other side branch) whereas the other guide wire 20 projects fer into the internal carotid artery (or other vessel). The bifurcated stent 80 is advanced along the guiide wires 20 by an over-the-wire catheter 60 or similar device such that when the stent 80 reaches the point of division at the juncture of the internal and external carotid arteries (or other bifurcated vessel), the arms of the bifurcated stent 80 divides. This division of the bifurcated stent 80 can be aided by using two filter/trap/occluders because of the retention force that they may have due to their impinging against the wall of the vessel. This will have a tendency to anchor the wire 20 and keep it from pulling out. This characteristic of the filter/trap/occluder is obviously of benefit elsewhere other than in FIG. 6 and even outside the scope of the present invention. One arm of the bifurcated stent will project into the internal carotid artery and the other arm into the external carotid artery withthe main portion of the stent remaining in the common and internal carotid arteries (or other bifurcated vessels). This is shown clearly in FIGS. 6B and 6C. After the stent is warmed in the case of a self-expanding stent or stent-graft (or otherwise enlarged) the guide wires 20 may be removed and the stent remains in position as shown in FIG. 6D.

Figure 4C:
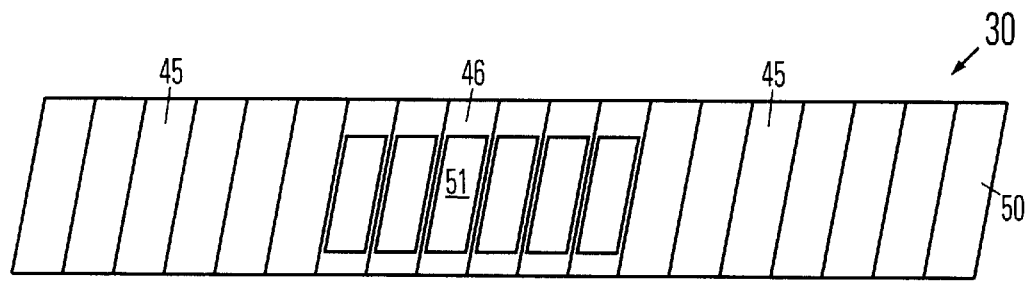
Figure 4D:
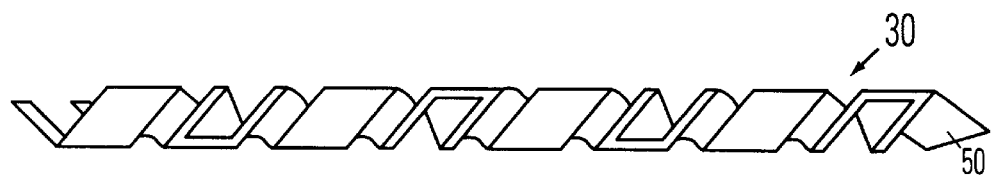

One such way of making the stent is to use flat wound wire 50 and coil it into a cylinder as shown in FIGS. 2, 4C and 4D. Prior to deployment and placement in the body, it would be longer and a smaller diameter than when deployed. Further, holes or windows 51 and/or 52 would be made in the flat part of the wire in such locations that when the stent is deployed and takes its shorter and larger diameter shape, the holes 51 or 52 would be oriented in such a fashion so that the stent could be place in such a way that the windows 51 & 52 of the stent would be aligned with respect to the bifurcated tributary (or side branch) and hence allow flow into or out of that tributary. It is understood that although the drawings indicate windows 51 & 52 only along one side of the stent or stent-graft, it would be simple to design windows circumferentially around the scaffold that would simplify placement of the device by the physician Alternatively, the multi-porous stent could be simply constructed out of round or flat wire that is programmed to take a particular shape upon enlargement. In other words, the wire would be coiled small for insertion, but when enlarged, the coils would be oriented close together where there is no side branch, and the space between the coils could have an increased distance between them at the bifurcation or side branch Then the space would decrease or diminish altogether on the other side of the side branch and be nested closer against one another again. This configuration is not illustrated in the drawings, but is readily understood by anyone skilled in the art.

The multi-porous stent can be expanded for deployment with an expandable balloon (e.g. balloon expandable stent) affixed to an intravascular catheter 60 or could be fabricated of a biocompatible shape-memory alloy (SMA, polymeric or metal). If it is made from a SMA, the stent would take a preferred shape when exposed to a temperature differential.

This temperature differential could be from room temperature (70° F.) to body temperature (98° F.) or higher. Any convenient temperature differential could be employed to expand the stent. For example, hot saline (=105–115° F.) could be injected into the lumen of the vessel where the stent is positioned and ready for deployment to force the SMA stent to expand and deploy. The warmed stent would remain in position maintaining its expanded shape with the help of body temperature. This could be accomplished using a thermal guide wire or catheter as well. Further, SMA could be used in combination with balloon deployment.

Another stent design may employ a braided material to form the stent body, such that the preferred lower porosity area has less braid (thread density) in the particular area and/or more dense braid in the area where flow or porosity is not required.

The CPS (Cerebral Protection System) or DPS (Distal Protection System) approach allows the interventionalist an easy, safe and less costly approach to treat carotid stenosis (or other bifurcated stenosis) in a least invasive manner. This is accomplished by first using a guide wire filter to trap plaque or blood clots from traveling downstream and causing stroke, death, etc. However, the need arises for a stent that can be deployed at a "bifuircation" which does not occlude the tributary/side branch at the bifurcation. In other words, a multi-porous or bifurcated stent or stent-graft allows scaffolding to occur at the bifurcation and still allow blood to flow in the main vessel as well as into the bifurcated tributary.

To safely deploy a vascular stent, the physician must first gain access to the vascular lumen then advance the distal end of the filter guide wire through the vessel until the fragment filter is positioned distal to blood flow. The interventionalist then deploys the filter which is constructed such that it will allow blood to flow through it but will trap 2–300 micron particles (or other particulate size that may be detrimental). The guide wire filter is a two-lumen system with a moveable braid on the distal end. Alternatively the braid could have an elastic membrane over it so that it occludes the vessel fully or partially. If full occlusion occurs (from a fully or partially sealed filter 41), the lumen could be 'washed' for particulate (emboli) similar to the way endarterectomies are washed before closing the artery. In this case the 'washing' would be done by flushing and irrigating the lumen and then with subsequent aspiration. This 'washing' may be repeated. When the two-hunen (42 & 43) filter 40 structure is pulled with respect to each other, the braid folds out in a round, ellipsoid, cone shape, etc. configuration. One side of the braid (the proximal end) may have large interstitial spaces and the other half may have small spaces that will trap clots and plaque.

Once deployed, the interventionist then slides the catheter 60 with the multi-porous stent 30 over the guide wire and advances the stent into position proximal to the fragment filter 40. Once in place, the multi-porous stent is deployed by expanding a balloon (not shown) thereunder to force the stent wall to expand within the vessel and be in correct orientation to the bifurcated tributary or side branch. Alternatively the stent 30 could be enlarged using thermal energy. When the multi-porous stent is successfully deployed, the guide wire filter is un-deployed into its original small orientation (with any clots or plaque particles trapped inside) and removed or otherwise obliterated.

Often a stent or stent-graft such as a braided stent is mounted on a catheter over an inflatable balloon. The stent is prevented from expanding until in proper position within the vessel whereupon the balloon is inflated, causing the braided stent to press against the intima (inner wall of the vessel). The balloon and filter are then deflated and retracted respectively and the removed leaving the stent within the vessel (s). It is noticed that the filter/trap/occluder can also be mounted onto the deployment catheter as opposed to a separate device. Alternatively, balloon angioplasty can be accomplished prior to inserting the stent to allow for easier placement of the stent and a subsequent larger diametrical result.

An in vitro model of the bifurcated carotid was designed and fabricated and a multi-porous stent and delivery system were developed. The multi-porous stent was deployed in the bifurcated area and proved to adequately provide scaffolding to prop open the common-internal carotid junction as well as continue to provide flow to the external carotid artery

What I claim is:

1. A device for the removal of particles from a lumen within the body comprising:

an outer, hollow tube having a tube distal end;

an inner member housed within the tube and having an inner member distal end positioned distally of the tube distal end;

a porous braided structure having a distal part secured to the inner member distal end and a proximal part secured to the tube distal end;

the braided structure movable from a contracted condition to an expanded condition by moving at least one of the tube and inner member distal ends towards the other; and the braided structure adapted to inhibit particles from moving completely through the braided structure when in the expanded condition.

2. The device as in claim 1 where said braided structure has a porous proximal side and a porous distal side.

3. The device as in claim 2 wherein said distal side has smaller sores than the proximal side.

4. The device as in claim 3 wherein said braided structure comprises a section of a tubular, porous braided structure having alternating first and second braided sections, said first braided sections, corresponding to said distal side, having pore sizes smaller than the second braided sections, corresponding to said proximal side.

5. The device as in claim 1 where said porous membrane is an elastic membrane.

6. The device as in claim 1 further comprising a porous membrane in contact with the braided structure, the membrane having smaller pores than the braided structure, whereby the braided structure and the porous membrane therewith are adapted to inhibit particles from moving completely through the braided structure when in the expanded condition.

7. A device for the removal of particles from a lumen within the body comprising:

an outer, hollow tube having a tube distal end;

an inner member housed within the tube and having an inner member distal end positioned distally of the tube distal end;

a porous braided structure having a porous proximal side, a porous distal side, a distal part secured to the inner member distal end and a proximal part secured to the tube distal end;

the braided structure movable from a contracted condition to an expanded condition by moving at least one of the tube and inner member distal ends towards the other;

a porous elastic membrane in contact with the porous distal side of the braided structure, the membrane having smaller pores than the braided structure; and the braided structure and porous membrane therewith adapted to inhibit particles from moving completely through the braided structure when in the expanded condition.

8. A device for the removal of particles from a lumen within the body comprising:

an outer, hollow tube having a tube distal end;

an inner member housed within the tube and having an inner member distal end positioned distally of the tube distal end;

a porous braided structure having a distal part secured to the inner member distal end and a proximal part secured to the tube distal end;

the braided structure being a temperature-sensitive shape memory material;

the braided structure movable from a contracted condition to an expanded condition by at least one of the following:

heating the temperature-sensitive braided material; and moving at least one of the tube and inner member distal ends towards the other; and the braided structure adapted to inhibit particles from moving completely through the braided structure when in the expanded condition.

9. A device for the removal of particles from a lumen within the body comprising:

an outer, hollow tube having a tube distal end;

an inner member housed within the tube and having an inner member distal end positioned distally of the tube distal end;

a porous braided structure having a porous proximal side, a porous and distal side, a distal part secured to the inner member distal end and a proximal part secured to the tube distal end;

the braided structure being a temperature-sensitive shape memory material;

the braided structure movable from a contracted condition to an expanded condition by at least one of the following:

heating the temperature-sensitive braided material; and moving at least one of the tube and inner member distal ends towards the other;

a porous elastic membrane in contact with the porous distal side of the braided structure, the membrane having smaller pores than the braided structure; and the braided structure and porous membrane therewith adapted to inhibit particles from moving completely through the braided structure when in the expanded condition.

* * * * *